United States Patent [19]

Higashio et al.

[11] Patent Number: 5,529,755
[45] Date of Patent: Jun. 25, 1996

[54] APPARATUS FOR MEASURING A GLUCOSE CONCENTRATION

[75] Inventors: Kimihiko Higashio, Kobe; Masahiro Ariizumi, Osaka, both of Japan

[73] Assignee: Minolta Co., Ltd., Osaka, Japan

[21] Appl. No.: 389,910

[22] Filed: Feb. 16, 1995

[30] Foreign Application Priority Data

Feb. 22, 1994 [JP] Japan .................................. 6-024187

[51] Int. Cl.$^6$ .................................................. G01N 21/59
[52] U.S. Cl. ........................... 422/82.09; 436/95; 128/633
[58] Field of Search ........................ 422/82.09; 436/95, 436/164; 128/633, 664; 356/39, 433–436; 250/339.04

[56] References Cited

U.S. PATENT DOCUMENTS

| | | | |
|---|---|---|---|
| 4,703,175 | 10/1987 | Salour et al. ........................... | 250/227 |
| 5,009,230 | 4/1991 | Hutchinson ............................. | 128/633 |
| 5,086,229 | 2/1992 | Rosenthal et al. . | |
| 5,137,023 | 8/1992 | Mendelson et al. .................... | 128/633 |
| 5,267,152 | 11/1993 | Yang et al. . | |
| 5,277,181 | 1/1994 | Mendelson et al. ..................... | 128/633 |
| 5,370,114 | 12/1994 | Wong et al. ............................. | 128/633 |

FOREIGN PATENT DOCUMENTS

| | | |
|---|---|---|
| 0160768 | 5/1984 | European Pat. Off. . |
| 3173535 | 7/1991 | Japan . |
| 440940 | 2/1992 | Japan . |
| 4332535 | 11/1992 | Japan . |

*Primary Examiner*—Jeffrey R. Snay
*Attorney, Agent, or Firm*—Price, Gess & Ubell

[57] ABSTRACT

A non-invasive glucose concentration measurement apparatus includes: a light source which projects at the sample radiation of a wavelength range including a wavelength at which absorption greatly changes with glucose concentration but does not greatly vary with temperature; a photosensor which receives the radiation which have been projected by the light source, and transmitted through or reflected by the sample, and generates an electrical signal corresponding to a through-transmitted or reflected level of the radiation of the wavelength; and a calculator which calculates a glucose concentration based on the electrical signal. A more accurate glucose concentration can be obtained without the influence of temperature.

14 Claims, 9 Drawing Sheets

APPARATUS FOR MEASURING A GLUCOSE CONCENTRATION

BACKGROUND OF THE INVENTION

The present invention relates to a glucose concentration measuring apparatus which measures a glucose concentration of a sample such as tissues of an organism using an optical device, and which can eliminate the syringe sampling of blood.

In recent years, there have been proposed so-called non-invasive type apparatuses for measuring a blood sugar level, which apparatuses are used to diagnose and care for diabetes patients. These apparatuses measure a glucose concentration in blood or an organism's tissues by use of an optical device without collecting blood or fracturing a part of the organism's tissues.

The basic concept of optical glucose concentration measurement is: Two kinds of radiation are projected to a sample to be measured. One kind is of radiation which is absorbed by glucose, and absorption of which changes according to glucose concentration. The other is of radiation which is hardly absorbed by glucose. A glucose concentration of a sample is obtained based on the energy of radiation transmitted through or diffused/reflected by the sample while excluding the influences by components other than glucose.

European Unexamined Patent Publication No. EP-A-160768 discloses: near infrared radiation having a wavelength $\lambda G$ of any of 1575 nm±15 nm, 1765±15 nm, 2100 nm±15 nm and 2270±15 nm is selected as radiation to be absorbed by glucose and near infrared radiation having a wavelength $\lambda R$ selected from a wavelength range between 1000 nm and 2700 nm is selected as radiation hardly to be absorbed by glucose.

According to the disclosure of EP-A-160768, radiation of a measurement spectral range including a wavelength $\lambda G$ and radiation of a reference spectral range including the wavelength $\lambda R$ are projected to a sample to be measured. Light energies transmitted through the sample are respectively received. An absorbed quantity of near infrared radiation of the measurement spectral range, namely a measurement value, and an absorbed quantity of near infrared radiation of the reference spectral range, namely a reference value, are compared so as to reduce the influence of errors caused by light absorption by substances other than glucose.

Further, Japanese Unexamined Patent Publication No. 3-173535 discloses a measuring method on the basis of the same concept as the above publication. Near infrared radiation of a wavelength range between 1600 nm and 1750 nm is used as radiation to be absorbed by glucose and near infrared radiation of a wavelength range between 1200 nm and 1300 nm is used as radiation not to be absorbed by glucose.

Moreover, Japanese Unexamined Patent Publication No. 3-146032 discloses non-invasive type method and apparatus for measuring a blood sugar level. According to this disclosure, radiation of a measurement wavelength range between, e.g., 1.3 μm and 1.9 μm is projected at a sample to be measured and a blood sugar level is calculated based on the obtained level of received radiation and a prestored verification curve.

Furthermore, U.S. Pat. No. 5,086,229 discloses, on the basis of the fact that a level of received measurement radiation differs depending upon temperature, more accurate measurement of glucose concentration by adding a factor, namely, a surface temperature of a sample to be measured into an operation expression used to calculate a glucose concentration.

There are also proposed measuring methods which, in order to measure the concentration of substances in blood more accurately, use a pulsation component and a variation resulting from an increased or reduced pressure (Japanese Unexamined Patent Publications Nos. 4-40940 and 4-332535).

The invention disclosed in U.S. Pat. No. 5,086,229 is capable of measuring a glucose concentration with the reduced influence of temperature because a temperature factor is taken into account. However, a special device for measuring surface temperature must be provided.

In addition, the surface temperature of an organism does not necessarily correspond with the temperature of blood or in the organism, or there may be no correlation therebetween.

Thus, it cannot be denied that there is an accuracy limit in measuring glucose concentration Further addition of a measurement factor caused by measuring the surface temperature of an organism complicates the processing for measurement data and a circuit therefor and adversely influences measurement accuracy.

SUMMARY OF THE INVENTION

It is an object of the present invention to provide a glucose concentration measuring apparatus which has overcome the problems residing in prior art.

It is another object of the present invention to provide a glucose concentration measuring apparatus which can eliminate the influences of temperature by taking into account a temperature characteristic in light absorption.

Accordingly, the present invention is directed to an apparatus for measuring a glucose concentration of a sample, the apparatus comprising: a first light source which projects at the sample radiation of a wavelength range including a first wavelength $\lambda 1$ at which absorption is dependent upon glucose concentration; a second light source which projects at the sample radiation of a wavelength range including a second wavelength $\lambda 2$ at which absorption has a temperature characteristic correlated with that in absorption of radiation of the first wavelength $\lambda 1$; a photosensor which receives the two kinds of radiation which have been projected by the first and second light sources, and transmitted through or reflected by the sample, and generates a first electrical signal corresponding to a through-transmitted or reflected level of the radiation of the first wavelength $\lambda 1$ and a second electrical signal corresponding to a through-transmitted or reflected level of the radiation of the second wavelength $\lambda 2$; and a calculator which calculates a glucose concentration based on the first and second electrical signals.

It may be preferable that the first wavelength $\lambda 1$ lies within a range between 1560 nm and 1760 nm and the second wavelength $\lambda 2$ lies within a range between 1440 nm and 1560 nm.

Also, it may be preferable that the first wavelength $\lambda 1$ lies within a range between 2080 nm and 2230 nm and the second wavelength $\lambda 2$ lies within a range between 2050 nm and 2080 nm.

It may be appreciated that the photosensor is provided with an optical filter for separately receiving the radiation of the wavelength range including the first wavelength $\lambda 1$ and the radiation of the wavelength range including the second wavelength $\lambda 2$.

It may be appreciated to further provide a pressing device which presses the sample. In this case, the photosensor may be made to generate first and second electrical signals in a state of the sample being not pressed and first and second electrical signals in another state of the sample being pressed. The calculator may be made to calculate a glucose concentration based on the first and second electrical signals in the non-pressed state and the first and second electrical signals in the pressed state. Also, the calculator may be made to calculate a glucose concentration in consideration of a variation in the through-transmitted or reflected radiation which is caused by pulsation of blood at a measured portion when the sample is an organism.

Also, the present invention is directed to an apparatus for measuring a glucose concentration of a sample, the apparatus comprising: a first light source which projects at the sample radiation of a wavelength range including a first wavelength $\lambda 1$ at which absorption greatly changes with glucose concentration but does not greatly vary with temperature; a second light source which projects at the sample radiation of a wavelength range including a second wavelength $\lambda 2$ at which absorption does not greatly change with glucose concentration and does not greatly vary with temperature; a photosensor which receives the two kinds of radiation which have been projected by the first and second light sources, and transmitted through or reflected by the sample, and generates a first electrical signal corresponding to a through-transmitted or reflected level of the radiation of the first wavelength $\lambda 1$ and a second electrical signal corresponding to a through-transmitted or reflected level of the radiation of the second wavelength $\lambda 2$; and a calculator which calculates a glucose concentration based on the first and second electrical signals.

The first wavelength $\lambda 1$ may lie within a range between 2155 nm and 2225 nm. The second wavelength $\lambda 2$ may lie within a range between 1200 nm and 1300 nm.

Further, the present invention is directed to an apparatus for measuring a glucose concentration of a sample, the apparatus comprising: a light source which projects at the sample radiation of a wavelength range including a first wavelength $\lambda 1$ at which absorption is dependent upon glucose concentration and a second wavelength $\lambda 2$ at which absorption has a temperature characteristic correlated with that in absorption of radiation of the first wavelength $\lambda 1$; a photosensor which receives the two kinds of radiation which have been projected by the light source, and transmitted through or reflected by the sample, and generates a first electrical signal corresponding to a through-transmitted or reflected level of the radiation of the first wavelength $\lambda 1$ and a second electrical signal corresponding to a through-transmitted or reflected level of the radiation of the second wavelength $\lambda 2$; and a calculator which calculates a glucose concentration based on the first and second electrical signals.

Further, the present invention is directed to an apparatus for measuring a glucose concentration of a sample, the apparatus comprising: a light source which projects at the sample radiation of a wavelength range including a first wavelength $\lambda 1$ at which absorption greatly changes with glucose concentration but does not greatly vary with temperature and a second wavelength $\lambda 2$ at which absorption does not greatly change with glucose concentration and does not greatly vary with temperature; a photosensor which receives the two kinds of radiation which have been projected by the light source, and transmitted through or reflected by the sample, and generates a first electrical signal corresponding to a through-transmitted or reflected level of the radiation of the first wavelength $\lambda 1$ and a second electrical signal corresponding to a through-transmitted or reflected level of the radiation of the second wavelength $\lambda 2$; and a calculator which calculates a glucose concentration based on the first and second electrical signals.

It may be preferable that the first wavelength $\lambda 1$ lies within a range between 2155 nm and 2225 nm while the second wavelength $\lambda 2$ lies within a range between 1200 nm and 1300 nm.

Moreover, the present invention is directed to an apparatus for measuring a glucose concentration of a sample, the apparatus comprising: a light source which projects at the sample radiation of a wavelength range including a wavelength which lies within a range between 2155 nm and 2225 nm, and at which absorption greatly changes with glucose concentration but does not greatly vary with temperature; a photosensor which receives the radiation which have been projected by the light source, and transmitted through or reflected by the sample, and generates an electrical signal corresponding to a through-transmitted or reflected level of the radiation of the wavelength $\lambda$; and a calculator which calculates a glucose concentration based on the electrical signal.

In the apparatus in which radiation of wavelength $\lambda 1$ where absorption is dependent upon glucose concentration and radiation of wavelength $\lambda 2$ where absorption has a temperature characteristic in correlation with that of radiation of wavelength $\lambda 1$ are used, a glucose concentration is obtained after a temperature correction is applied based on levels of received radiation of wavelengths $\lambda 1$ and $\lambda 2$. Accordingly, a variation in the level of received radiation of wavelength $\lambda 1$ resulting from a temperature change can be canceled. Thus, the glucose concentration can be measured with better accuracy without additionally providing a separate device to measure temperature of the sample.

Also, in the apparatus in which radiation of a first wavelength $\lambda 1$ at which absorption greatly changes with glucose concentration but does not greatly vary with temperature and radiation of a second wavelength $\lambda 2$ at which absorption does not greatly change with glucose concentration and does not greatly vary with temperature are used to measure a glucose concentration, it will be possible to eliminate the influence of the organism's tissues such as skins and bones as well as the influence of temperature.

These and other objects, features and advantages of the present invention will become more apparent upon a reading of the following detailed description and accompanying drawings.

DETAILED DESCRIPTION OF THE PREFERRED EMBODIMENTS OF THE INVENTION

Figure 1:
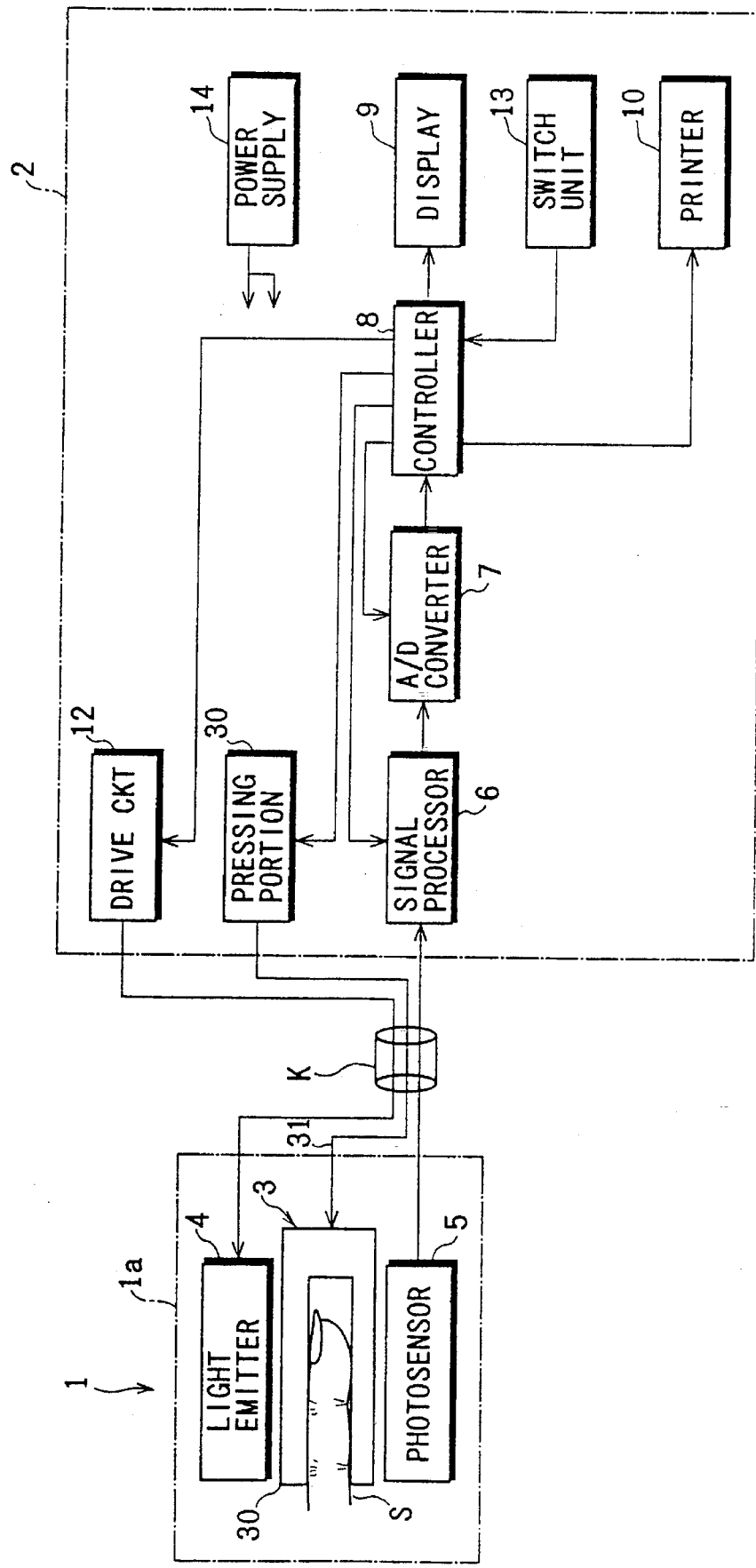
FIG. 1 is a block diagram of a glucose concentration measuring apparatus according to the invention.

An exemplified non-invasive type glucose concentration measuring apparatus according to the invention will be described with reference to a block diagram of FIG. 1.

The measuring apparatus is adapted to measure a glucose concentration in blood without additionally collecting blood or fracturing a tissues. The measuring apparatus is provided with a measuring probe 1 and an apparatus main body 2. The measuring probe 1 and the apparatus main body 2 are connected with each other by way of a cable K.

The measuring probe 1 includes a housing 1a, in which there are provided a cuff 3 for pinching and pressing a sample to be measured, a light emitter 4 and a photosensor 5 disposed at opposed positions with the sample pinched by the cuff 3 therebetween.

The cuff 3 includes a pressing portion 30 of transparent flexible material which has at least two opposed sides defining a hollow space, and a tube 31 which connects the pressing portion 30 and a cuff pressure control circuit 11 for supplying air to the pressing portion 30. Upon receipt of air from the cuff pressure control circuit 11, the pressing portion 30 inflates to press a sample S to be measured such as a finger, earlobe, wrist, instep and back of a newborn baby or infant, or other organism's tissues.

The light emitter 4 includes a light emitter diode or laser diode, and is adapted to project radiation of wavelength ranges at least including a wavelength $\lambda 1$ used to measure a glucose concentration and a reference wavelength $\lambda 2$ used for a temperature correction, respectively. The photosensor 5 receives light energy transmitted through the sample S and photoelectrically converts the received light energy to be output to the apparatus main body 2.

The photosensor 5 is also provided with an optical filter including photoconductive cells for separately detecting the, radiation of the wavelength range including the wavelength $\lambda 1$ and the radiation of the wavelength range of a specified width including the reference wavelength $\lambda 2$. The light emitter 4 and the photosensor 5 are disposed in such positions that light emission and light reception are not hindered by the pressing portion 30.

The light emitter 4 may include a xenon lamp, halogen lamp, or like device for projecting radiation of a wide wavelength range, and an optical filter so that only radiation of wavelengths $\lambda 1$ and $\lambda 2$ are projected through the optical filter. Further, the photosensor 5 may be disposed adjacent the light emitter 4 so as to receive the light emitted from the light emitter 4, diffused or reflected by the sample S. Furthermore, the light emitter 4 and the photosensor 5 may be so disposed as to face the inner surfaces of the pressing portion 30.

The apparatus main body 2 is provided with a signal processor 6, an analog-to-digital (A/D) converter 7, and a controller 8. The signal processor 6 amplifies signals representing the received radiation of wavelengths $\lambda 1$ and $\lambda 2$ which is output from the photosensor 5 and filters the amplified signals (removes noises of the amplified signals) to be output to the A/D converter 7. The A/D converter 7 converts the analog signals from the signal processor 6 into digital signals and outputs the resulting signals, each signal representing a quantity of radiation transmitted through the sample S, to the controller 8. The controller 8 calculates a glucose concentration based on the quantities of transmitted radiation of wavelengths $\lambda 1$ and $\lambda 2$ and centrally controls respective elements of the apparatus main body 2 in accordance with a program for measuring a glucose concentration.

The apparatus main body 2 is further provided with a display 9, a printer 10, the cuff pressure control circuit 11, a light emitter drive circuit 12, an operation switch unit 13 and a power supply unit 14. The display 9 displays a variety of information including glucose concentration in blood and information that the glucose concentration is in excess of a predetermined level and, if necessary, a warning. The printer 10 prints the glucose concentration and other information. The control circuit 11 controls supply of air to the cuff 3 so as to control a pressing force exerted on the sample S. The drive circuit 12 causes the light emitter 4 to emit radiation. The operation switch unit 13 has a variety of switches including a measurement start switch which is operated to start measurement of glucose concentration and a print start switch which is operated to start the printing. The power supply unit 14 supplies power to the respective elements of the apparatus main body 2.

The controller 8 calculates the glucose concentration in the sample S based on the respective quantities of transmitted radiation of wavelengths $\lambda 1$ and $\lambda 2$ which are sent from the A/D converter 7. The controller 8 includes memory for storing the respective quantities of transmitted radiation sent from the A/D converter 7 and a control program.

A glucose concentration Cg can be calculated by using a double regression function. A quantity of radiation of wavelength $\lambda$ which have transmitted through blood is expressed as Equation (1).

$$I_\lambda = I_{0\lambda} \cdot 10^{-\{\epsilon w\lambda + \epsilon g\lambda \cdot C_g + \epsilon t\lambda \cdot f(\Delta t)\}d} \quad \text{[Equation 1]}$$

where I denotes a quantity of transmitted radiation, Io denotes a quantity of incident radiation, $\lambda$ denotes wavelength, $\epsilon w$ denotes an absorption coefficient of blood, $\epsilon g$ denotes an absorption coefficient of glucose, Cg denotes glucose concentration, $\epsilon t$ denotes a temperature coefficient. f denotes an absorption function with respect to temperature, $\Delta t$ denotes a difference from a reference temperature, and d denotes length of an optical path.

Hereafter, measurements under a variety of conditions are described.

[1] IN THE CASE WHERE Cg. $\Delta t$ ARE UNKNOWN (LENGTH d OF THE OPTICAL PATH IS CONSTANT)

The quantities of transmitted radiation of wavelengths $\lambda 1$ and $\lambda 2$ are expressed as in Equation (2) from Equation (1).

$$I_{\lambda 1} = I_{0\lambda 1} \cdot 10^{-\{\epsilon w\lambda 1 + \epsilon g\lambda 1 \cdot C_g + \epsilon t\lambda 1 \cdot f(\Delta t)\}d} \quad \text{[Equation 2]}$$

$$I_{\lambda 2} = I_{0\lambda 2} \cdot 10^{-\{\epsilon w\lambda 2 + \epsilon g\lambda 2 \cdot C_g + \epsilon t\lambda 2 \cdot f(\Delta t)\}d}$$

When Equation (2) is solved for the glucose concentration Cg, Cg is obtained as Equation (3). Here, it should be noted that $\log(I_{\lambda 1}/I_{0\lambda 1})$ is absorption at the wavelength $\lambda 1$.

$$Cg = -[\{\epsilon_{t\lambda 2} \cdot \log(I_{\lambda 1}/I_{0\lambda 1}) - \epsilon_{t\lambda 1} \cdot \log(I_{\lambda 2}/I_{0\lambda 2})\}/d - (\epsilon_{\omega\lambda 1} \cdot \epsilon_{t\lambda 2} - \epsilon_{\omega\lambda 2} \cdot \epsilon_{t\lambda 1})]/(\epsilon_{g\lambda 1} \cdot \epsilon_{t\lambda 2} - \epsilon_{g\lambda 2} \cdot \epsilon_{t\lambda 1})$$  [Equation 3]

Equation (3) can be rewritten into a general equation as in Equation (4).

$$Cg = K_1 \cdot \log(I_{\lambda 1}/I_{0\lambda 1}) + K_2 \cdot \log(I_{\lambda 2}/I_{0\lambda 2}) + K_3$$  [Equation 4]

The glucose concentration Cg is calculated by substituting values K1 to K3 of Equation (5) into Equation (4).

$$K_1 = -\epsilon_{t\lambda 2}/(\epsilon_{g\lambda 1} \cdot \epsilon_{t\lambda 2} - \epsilon_{g\lambda 2} \cdot \epsilon_{t\lambda 1}) \cdot d$$

$$K_2 = -\epsilon_{t\lambda 1}/(\epsilon_{g\lambda 1} \cdot \epsilon_{t\lambda 2} - \epsilon_{g\lambda 2} \cdot \epsilon_{t\lambda 1}) \cdot d$$

$$K_3 = (\epsilon_{\omega\lambda 1} \cdot \epsilon_{t\lambda 2} - \epsilon_{\omega\lambda 2} \cdot \epsilon_{t\lambda 1})/(\epsilon_{g\lambda 1} \cdot \epsilon_{t\lambda 2} - \epsilon_{g\lambda 2} \cdot \epsilon_{t\lambda 1}) \cdot d$$  [Equation 5]

[2] IN THE CASE WHERE Cg, $\Delta t$, d ARE UNKNOWN

From Equation (1), quantities of transmitted radiation of wavelengths $\lambda 1$, $\lambda 2$ and $\lambda 3$ are expressed as Equation (6).

$$I_{\lambda 1} = I_{0\lambda 1} \cdot 10^{-\{\epsilon_{\omega\lambda 1} + \epsilon_{g\lambda 1} \cdot Cg + \epsilon_{t\lambda 1} \cdot f(\Delta t)\}d}$$

$$I_{\lambda 2} = I_{0\lambda 2} \cdot 10^{-\{\epsilon_{\omega\lambda 2} + \epsilon_{g\lambda 2} \cdot Cg + \epsilon_{t\lambda 2} \cdot f(\Delta t)\}d}$$

$$I_{\lambda 3} = I_{0\lambda 3} \cdot 10^{-\{\epsilon_{\omega\lambda 3} + \epsilon_{g\lambda 3} \cdot Cg + \epsilon_{t\lambda 3} \cdot f(\Delta t)\}d}$$  [Equation 6]

When Equation (6) is solved for the glucose concentration Cg, Cg is obtained as shown in Equation (7).

$$Cg = \{(\epsilon_{\omega\lambda 2} \cdot \epsilon_{t\lambda 3} - \epsilon_{\omega\lambda 3} \cdot \epsilon_{t\lambda 2}) \cdot \log(I_{\lambda 1}/I_{0\lambda 1}) + (\epsilon_{\omega\lambda 3} \cdot \epsilon_{t\lambda 1} - \epsilon_{\omega\lambda 1} \cdot \epsilon_{t\lambda 3}) \cdot \log(I_{\lambda 2}/I_{0\lambda 2}) + (\epsilon_{\omega\lambda 1} \cdot \epsilon_{t\lambda 2} - \epsilon_{\omega\lambda 2} \cdot \epsilon_{t\lambda 1}) \cdot \log(I_{\lambda 3}/I_{0\lambda 3})\}/\{(\epsilon_{g\lambda 2} \cdot \epsilon_{t\lambda 3} - \epsilon_{g\lambda 3} \cdot \epsilon_{t\lambda 2}) \cdot \log(I_{\lambda 1}/I_{0\lambda 1}) + (\epsilon_{g\lambda 3} \cdot \epsilon_{t\lambda 1} - \epsilon_{g\lambda 1} \cdot \epsilon_{t\lambda 3}) \cdot \log(I_{\lambda 2}/I_{0\lambda 2}) + (\epsilon_{g\lambda 1} \cdot \epsilon_{t\lambda 2} - \epsilon_{g\lambda 2} \cdot \epsilon_{t\lambda 1}) \cdot \log(I_{\lambda 3}/I_{0\lambda 3})\}$$  [Equation 7]

Equation (7) can be rewritten into a general equation as in Equation (8).

$$Cg = \{k_1 \cdot \log(I_{\lambda 1}/I_{0\lambda 1}) + k_2 \cdot \log(I_{\lambda 2}/I_{0\lambda 2}) + k_3 \cdot \log(I_{\lambda 3}/I_{0\lambda 3})\}/\{K_1 \cdot \log(I_{\lambda 1}/I_{0\lambda 1}) + K_2 \cdot \log(I_{\lambda 2}/I_{0\lambda 2}) + K_3 \cdot \log(I_{\lambda 3}/I_{0\lambda 3})\}$$  [Equation 8]

tuting values K1 to K3 and k1 to k3 of Equation (9) into Equation (8).

$$K_1 = \epsilon_{g\lambda 2} \cdot \epsilon_{t\lambda 3} - \epsilon_{g\lambda 3} \cdot \epsilon_{t\lambda 2}$$

$$K_2 = \epsilon_{g\lambda 3} \cdot \epsilon_{t\lambda 1} - \epsilon_{g\lambda 1} \cdot \epsilon_{t\lambda 3}$$

$$K_3 = \epsilon_{g\lambda 1} \cdot \epsilon_{t\lambda 2} - \epsilon_{g\lambda 2} \cdot \epsilon_{t\lambda 1}$$

$$k_1 = \epsilon_{\omega\lambda 2} \cdot \epsilon_{t\lambda 3} - \epsilon_{\omega\lambda 3} \cdot \epsilon_{t\lambda 2}$$

$$k_2 = \epsilon_{\omega\lambda 3} \cdot \epsilon_{t\lambda 1} - \epsilon_{\omega\lambda 1} \cdot \epsilon_{t\lambda 3}$$

$$k_3 = \epsilon_{\omega\lambda 1} \cdot \epsilon_{t\lambda 2} - \epsilon_{\omega\lambda 2} \cdot \epsilon_{t\lambda 1}$$  [Equation 9]

If the wavelengths $\lambda 1$, $\lambda 2$ and $\lambda 3$ are selected as follows:

$\lambda 1$: glucose absorption (YES), temperature characteristic (YES)

$\lambda 2$: glucose absorption (NO) temperature characteristic (YES)

$\lambda 3$: glucose absorption (NO) temperature characteristic (NO),

Equation (8) can be written plainly as Equation (10) since $\epsilon g\lambda 2 = \epsilon g\lambda 3 = \epsilon t\lambda 3 = 0$.

$$Cg = \{k_1' \cdot \log(I_{\lambda 1}/I_{0\lambda 1}) = k_2' \cdot \log(I_{\lambda 2}/I_{0\lambda 2}) = k_3' \cdot \log(I_{\lambda 3}/I_{0\lambda 3})\}/k_3 \cdot \log(I_{\lambda 3}/I_{0\lambda 3})\}$$  [Equation 10]

[3] IN THE CASE WHERE AN UNNEGLIGIBLE QUANTITY OF INTERFERENCE SUBSTANCES EXIST IN BLOOD

In this case., Equation (1) can be expressed as in Equation (11).

$$I_\lambda = 10^{-\{\epsilon_{\omega\lambda} + \epsilon_g\lambda \cdot Cg + \epsilon_t\lambda \cdot f(\Delta t) + \epsilon_x\lambda\}d}$$  [Equation 11]

where $\epsilon x$ denotes an absorption coefficient of interference substances.

When Equation (11) is solved for the glucose concentration Cg similar to the above, Equation (12) can be obtained in accordance with which the glucose concentration Cg is calculated.

$$Cg = \{k_1 \cdot \log(I_{\lambda 1}/I_{0\lambda 1}) + \ldots + k_4 \cdot \log(I_{\lambda 4}/I_{0\lambda 4})\}/\{K_1 \cdot \log(I_{\lambda 1}/I_{0\lambda 1}) + \ldots + K_4 \cdot \log(I_{\lambda 4}/I_{0\lambda 4})\}$$  [Equation 12]

When the quantity of interference substances is further increased, the glucose concentration Cg can be calculated using Equation (13) in which the number of wavelengths used for measurement is increased.

$$Cg = \{k_1 \cdot \log(I_{\lambda 1}/I_{0\lambda 1}) + \ldots + k_n \cdot \log(I_{\lambda n}/I_{0\lambda n})\}/\{K_1 \cdot \log(I_{\lambda 1}/I_{0\lambda 1}) + \ldots + K_n \cdot \log(I_{\lambda n}/I_{0\lambda n})\}$$  [Equation 13]

[4] IN THE CASE WHERE INFLUENCE OF PARTS OTHER THAN BLOOD IS CONSIDERED

In this case, Equation (1) can be expressed as in Equation (14).

$$I_\lambda = I_{0\lambda} \cdot F_\lambda \cdot 10^{-\{\epsilon_{\omega\lambda} \epsilon_g\lambda \cdot Cg + \epsilon_t\lambda \cdot f(\Delta t)\}d}$$  [Equation 14]

where $F_\lambda$ denotes transmittance of parts other than blood.

From Equation (14). Equation (15) corresponding to Equation (4) in the case [1] is obtained, and the glucose concentration Cg is calculated in accordance with Equation (15).

$$Cg = K_1 \cdot \log(I_{\lambda 1}/I_{0\lambda 1}) + K_2 \cdot \log(I_{\lambda 2}/I_{0\lambda 2}) + K_3'$$  [Equation 15]

$$K_3' = K_3 - (K_1 \cdot \log F_{\lambda 1} + K_2 \cdot \log F_{\lambda 2})$$

Equation (16) corresponding to Equation (8) in the case [2] is obtained, and the glucose concentration Cg is calculated in accordance with Equation (16).

$$Cg = \{k_1 \cdot \log(I_{\lambda 1}/I_{0\lambda 1}) + k_2 \cdot \log(I_{\lambda 2}/I_{0\lambda 2}) + k_3 \cdot \log(I_{\lambda 3}/I_{0\lambda 3}) + k_4\}/\{K_1 \cdot \log(I_{\lambda 1}/I_{0\lambda 1}) + K_2 \cdot \log(I_{\lambda 2}/I_{0\lambda 2}) + K_3 \cdot \log(I_{\lambda 3}/I_{0\lambda 3}) + K_4\}$$  [Equation 16]

$$K_4 = -(K_1 \cdot \log F_{\lambda 1} + K_2 \cdot \log F_{\lambda 2} + K_3 \cdot \log F_{\lambda 3})$$

$$k_4 = -(k_1 \cdot \log F_{\lambda 1} + k_2 \cdot \log F_{\lambda 2} + k_3 \cdot \log F_{\lambda 3})$$

Equation (17) corresponding to Equation (13) in the case [3] is obtained, and the glucose concentration Cg is calculated in accordance with Equation (17).

$$Cg = \{k_1 \cdot \log(I_{\lambda 1}/I_{0\lambda 1}) + \ldots + k_n \cdot \log(I_{\lambda n}/I_{0\lambda n}) + k_{n+1}\}/\{K_1 \cdot \log(I_{\lambda 1}/I_{0\lambda 1}) + \ldots + K_n \cdot \log(I_{\lambda n}/I_{0\lambda n}) + K_{n+1}\}$$  [Equation 17]

$$K_{n+1} = -(K_1 \cdot \log F_{\lambda 1} + \ldots + K_n \cdot \log F_{\lambda n}) = -\sum_{i=1}^{n} (K_1 \cdot \log F_{\lambda 1})$$

$$k_{n+1} = -(k_1 \cdot \log F_{\lambda 1} + \ldots + k_n \cdot \log F_{\lambda n}) = -\sum_{i=1}^{n} (k_1 \cdot \log F_{\lambda 1})$$

Here, the wavelength λ1 used to measure glucose concentration and the reference wavelength λ2 used for a temperature correction are described. It is preferable in terms of accuracy in measuring glucose concentration to select as the wavelength λ1 a wavelength which causes the absorption greatly to vary with glucose concentration. Accordingly, radiation of such a wavelength that are easily absorbed by glucose, i.e., that are maximally absorbed by glucose should be selected. In some range of wavelengths, the absorption is likely to greatly change with temperature. Accordingly, it is necessary to prevent an error in a measurement value resulting from a temperature change by performing a temperature correction.

Next, the principle of correcting glucose concentration will be described in detail with reference to FIGS. 4 to 10.

Figure 4:
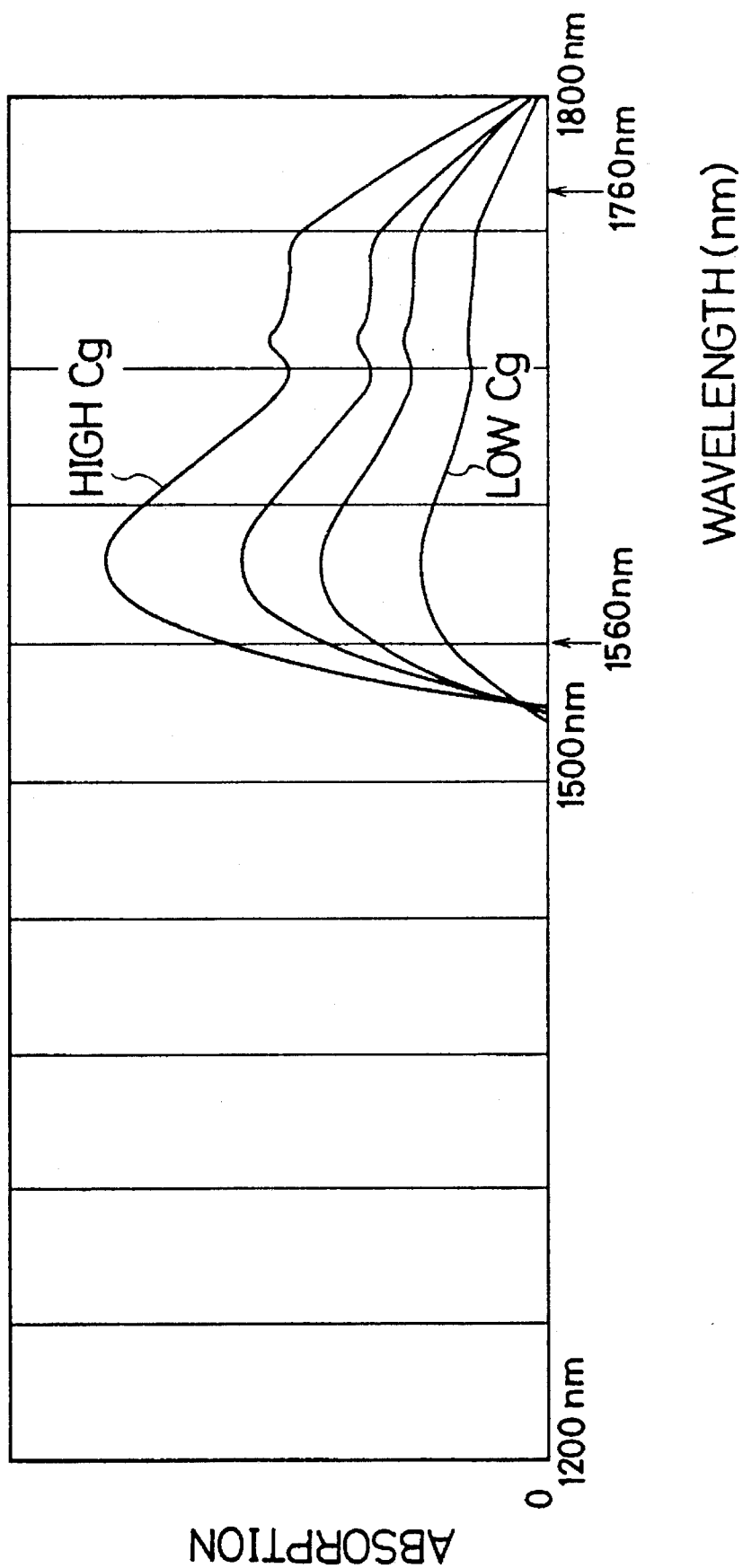
FIG. 4 is a graph showing an absorption characteristic of glucose solution with respect to radiation of a wavelength range between 1200 and 1800 nm.
Figure 5:
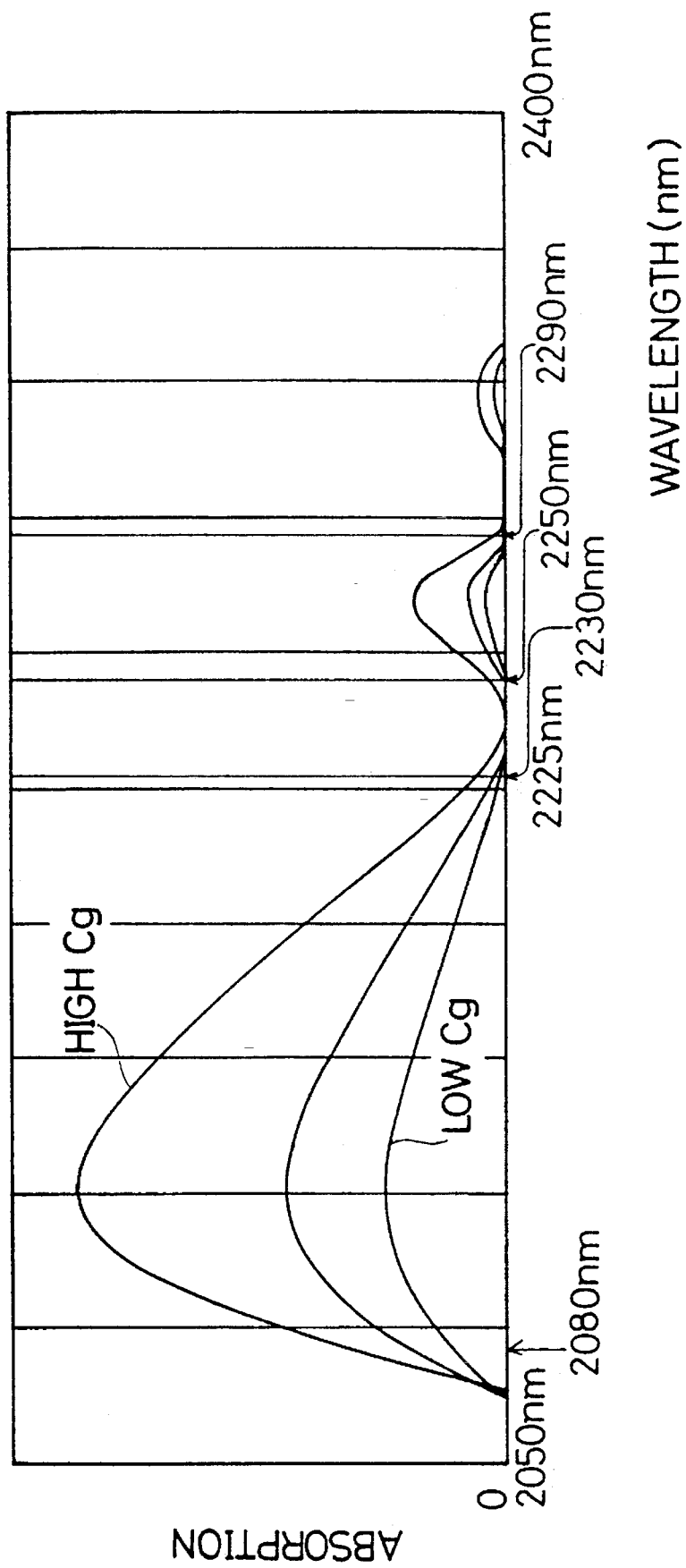
FIG. 5 is a graph showing an absorption characteristic of glucose solution with respect to radiation of a wavelength range between 2050 and 2400 nm.

FIGS. 4 and 5 show a variation where the absorption of a glucose solution increases as the glucose concentration increases.

In FIGS. 4 and 5, the horizontal axis represents the wavelength and the vertical axis represents the absorption of a glucose solution. The glucose solution strongly absorbs near infrared radiation of a wavelength range between 1560 nm and 1760 nm, peaked in the neighborhood of 1600 nm. In this wavelength range, the absorption of the glucose solution increases as the concentration thereof is increased.

It is also seen that the glucose solution absorbs near infrared radiation of wavelength ranges between 2080 nm and 2230 nm, and between 2250 nm and 2290 nm. In this wavelength range, the absorption of the glucose solution increases as the concentration thereof is increased.

Figure 6:
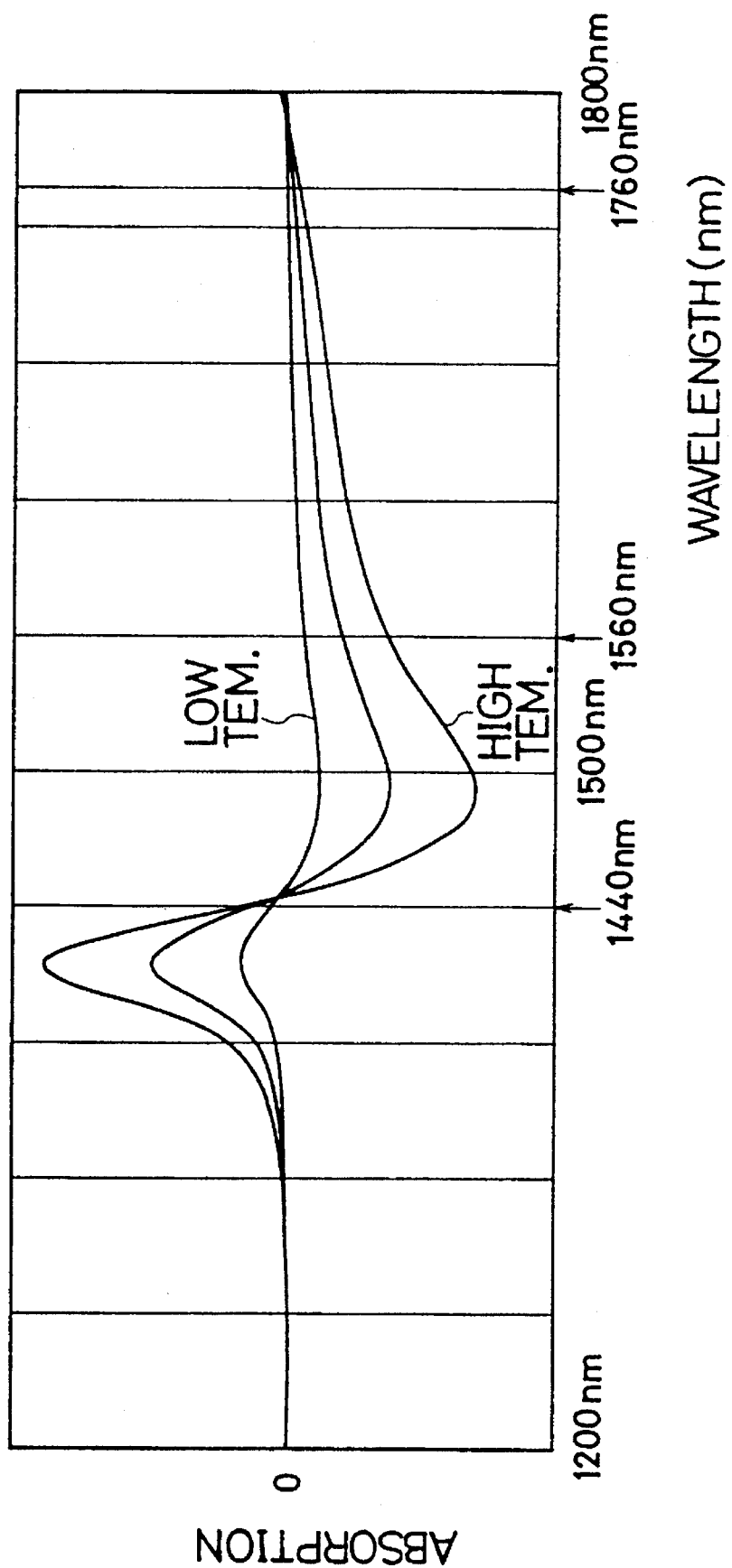
FIG. 6 is a graph showing a temperature characteristic of glucose solution in absorption of radiation of a wavelength range between 1200 and 1800 nm.
Figure 7:
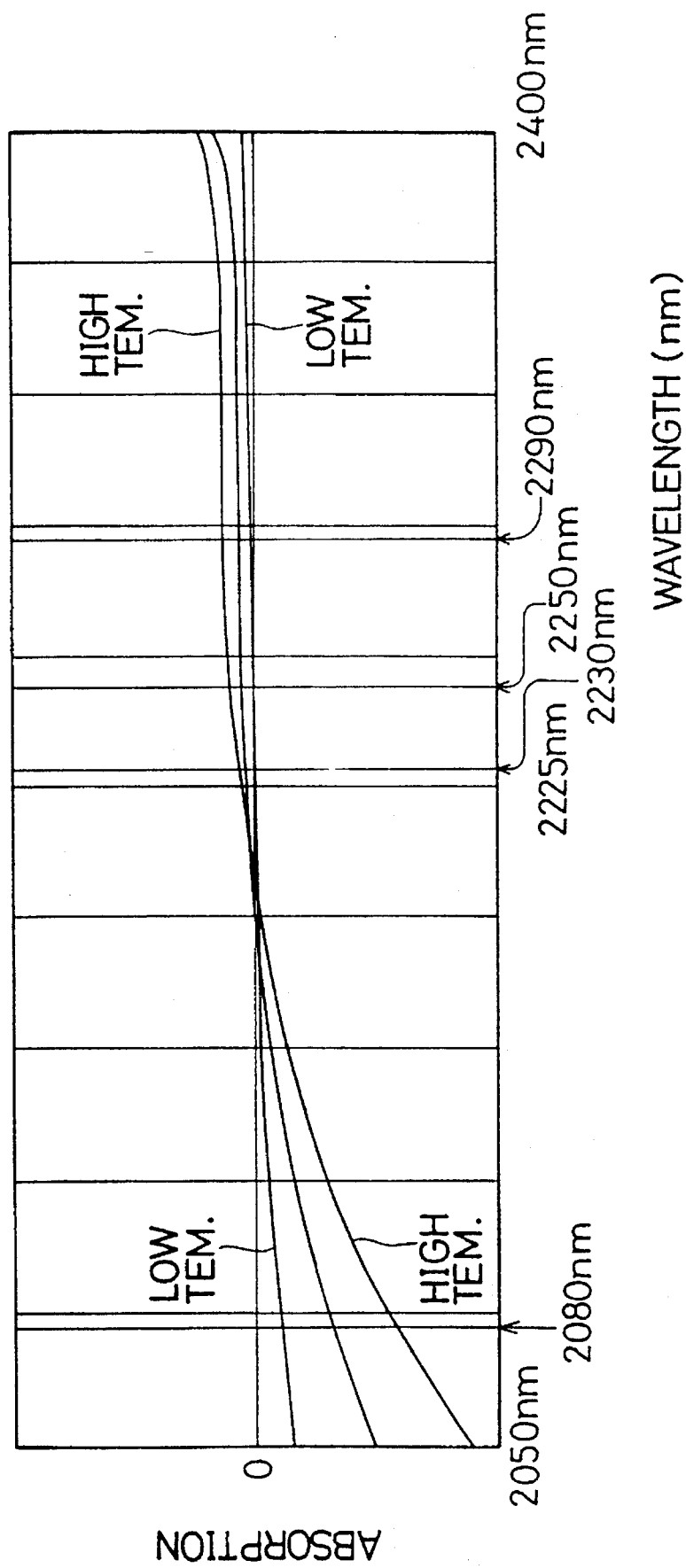
FIG. 7 is a graph showing a temperature characteristic of the glucose solution in absorption of radiation of a wavelength range between 2050 and 2400 nm.
Figure 8A:
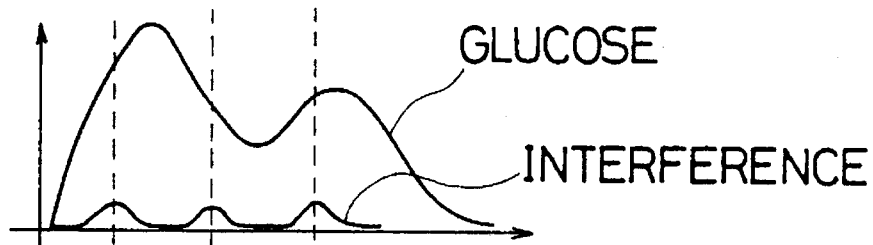
FIGS. 8A to 8E are graphs each showing an absorption curve of interference substances in relation to an absorption curve of glucose, especially showing a change in the absorption of the interference substances over time.
Figure 8B:
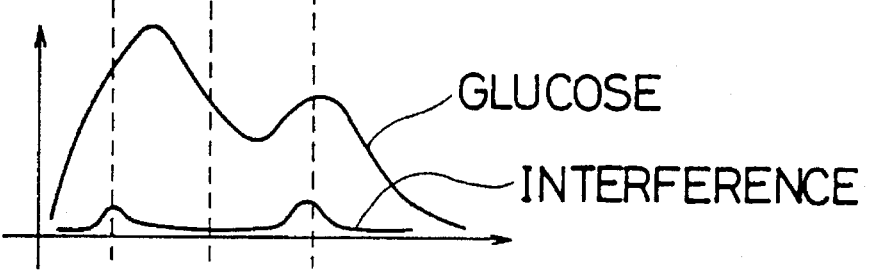
Figure 8C:
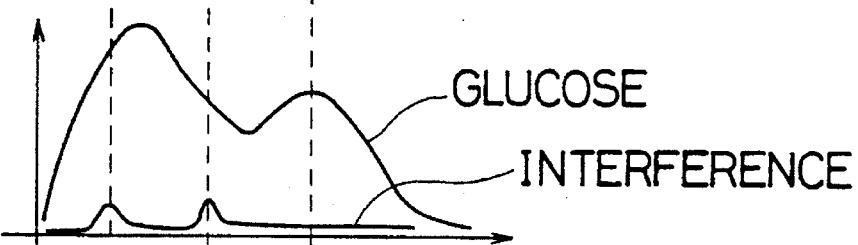
Figure 8D:
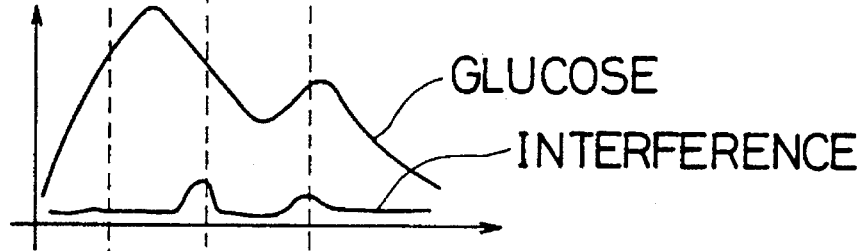
Figure 8E:
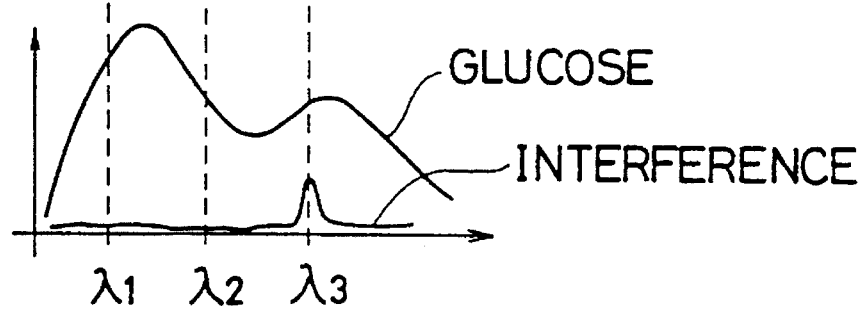

FIGS. 6 and 7 show a relative absorption characteristic of the glucose solution when the concentration of the glucose solution is held constant with temperature as a parameter. In these figures, the horizontal axis represents the wavelength and the vertical axis whose scale is enlarged in comparison with FIGS. 4 and 5 represents differences in absorption at various temperatures from the absorption at a low temperature as a reference temperature.

FIGS. 6 and 7 show a variation in absorption when temperature is changed from a specified low temperature as a reference temperature with glucose concentration constant ("0" line in these figures). Absorbance approaches to the "0" line as temperature approaches the reference low temperature.

The absorption for near infrared radiation of a wavelength range between 1440 nm and 1560 nm and that for near infrared radiation of a wavelength range between 1560 nm and 1760 nm where the absorption of glucose solution high (see FIG. 4) have substantially an equal correlation with respect to temperature. The absorption for near infrared radiation of the wavelength range between 1440 nm and 1560 nm hardly varies with glucose concentration as shown in FIG. 4.

Further, the absorption for near infrared radiation of a wavelength range between 2050 nm and 2080 nm and that for near infrared radiation of a wavelength range between 2080 nm and 2230 nm where the absorption of the glucose solution is high (see FIG. 5) and in a wavelength range between 2250 nm and 2290 nm have substantially an equal correlation with respect to temperature. The absorption for near infrared radiation of the wavelength range between 2050 nm and 2080 nm hardly varies with glucose concentration as shown in FIG. 5. A temperature characteristic in the wavelength range between 2050 nm and 2080 nm is negatively in correlation with that in the wavelength range between 2250 nm and 2290 nm.

Accordingly, it will be seen that the temperature correction can be performed by using radiation of wavelength λ2 for which absorption varies hardly with glucose concentration but varies with temperature and which lies within a wavelength range which provides a temperature characteristic in correlation with that of wavelength λ1 which provides a high absorption.

Specifically, as seen in FIG. 4, near infrared radiation of a wavelength range between 1560 nm and 1760 nm is strongly absorbed in the glucose solution peaked at a wavelength of 1600 nm. Accordingly the wavelength λ1 where the radiations are strongly absorbed by glucose is selected from the wavelength range between 1560 nm and 1760 nm. The wavelength λ1 may be selected from a wavelength range between 2080 nm and 2230 nm where high light absorption is seen and from a wavelength range between 2250 nm and 2290 nm where relatively high absorption is seen as shown in FIG. 5.

On the other hand, as shown in FIG. 4 and 6, the absorption of the near infrared radiation of a wavelength range between 1440 nm and 1560 nm does not greatly vary with glucose concentration. As seen from FIG. 6, the absorption in the wavelength range between 1440 nm and 1560 nm has a substantially equal correlation with respect to temperature with that in the wavelength range between 1560 nm and 1760 nm. Accordingly, the wavelength λ2 for the wavelength λ1 selected from the wavelength range between 1560 nm and 1760 nm is selected from the wavelength range between 1440 nm and 1560 nm.

Further, as shown in FIGS. 5 and 7, the absorption of the near infrared radiation of a wavelength range between 2050 nm and 2080 nm does not greatly vary with glucose concentration. As seen from FIG. 7, the absorption in the wavelength range between 2050 nm and 2080 nm has a substantially equal correlation with respect to temperature with that in the wavelength range between 2080 nm and 2230 nm. Accordingly, the wavelength λ2 for the wavelength λ1 selected from the wavelength range between 2080 nm and 2230 nm is selected from the wavelength range between 2050 nm and 2080 nm.

Furthermore the absorption in the wavelength range between 2050 nm and 2080 nm has a substantially equal correlation with respect to a temperature change with that in the wavelength range between 2250 nm and 2290 nm. Accordingly, the wavelength λ2 where glucose absorption is low is selected from the wavelength range between 2050 nm and 2080 nm for the wavelength μ1 selected from the wavelength range between 2250 nm and 2290 nm. It should be noted that the temperature characteristic in the wavelength range between 2050 nm and 2080 nm is negatively in correlation with that in the wavelength range between 2250 nm and 2290 nm.

The glucose concentration Cg obtained using the specific wavelengths λ1 and λ2 may be defined as Cg=F (λ1, λ2), for example, Cg=F (1595 nm, 1535 nm) where λ1 and λ2 are 1595 nm and 1535 nm respectively.

In addition to the above case where a specific single wavelength is selected, it is also possible to assume as a single wavelength an average of an entire wavelength range where glucose absorption can be seen. For example, glucose absorption can be seen in an entire wavelength range between 1530 nm and 1800 nm. If an average absorption of this wavelength range is assumed to be an absorption corresponding to the average wavelength of the wavelength range, the wavelength range can be considered to be a single wavelength. Further, if an average absorption of the temperature correction wavelength range is assumed to be an absorption corresponding to the average wavelength of the temperature correlation wavelength range, the temperature correction wavelength range can also be considered to be a signal wavelength. In the above example, the glucose concentration Cg can be defined as Cg=F (1560 nm to 1760 nm, 1300 nm to 1440 nm). The widths of the wavelength ranges may be larger or smaller than those in the above example.

It should be noted that in this specification, the wavelengths $\lambda 1$ and $\lambda 2$ refer to the wavelength ranges as well as the single wavelengths.

The use of a wavelength range has the following advantages:

(1) In actual measurement, radiation transmitted through a sample to be measured is measured by a detector. If radiation is excessively absorbed by the sample, a quantity of radiation of a single wavelength received by the detector may be below a lower limit of a detectable quantity range of radiation of the detector. This may be dealt with by increasing a quantity of radiation to be incident upon the sample but a light source has a limited light emitting performance. Accordingly, by using radiation of a wavelength range having a specified width instead of radiation of a single wavelength, a sufficient quantity of radiation can be assured.

(2) When a sample to be measured is an organism, for example, the sample contains, depending upon components of the organism's tissues a variety of interference substances, which are detected as noises. The absorption of glucose contains noises as shown in FIGS. 8A to 8E due to, for example, a change resulting from movement of the sample itself or a change of the sample over time. FIGS. 8A to 8E show absorption curves of interference substances in relation to absorption curves of glucose, especially showing an example of a change in the absorption of interference substances over time. When specific single wavelengths, e.g., wavelengths $\lambda 1$, $\lambda 2$ and $\lambda 3$ are selected as measurement wavelengths, absorption irregularly changes over time at the measurement wavelengths as seen from FIGS. 8A to 8E. Accordingly, the presence of noises during measurement causes large errors. By using a wide wavelength range as a measurement wavelength, the influence of errors resulting from the noises can be considerably reduced because errors are treated as a ratio to an entire area of the wavelength range instead of as a ratio to an area of the individual measurement wavelength. As a result, measurement can be conducted with sufficient accuracy.

Figure 9:
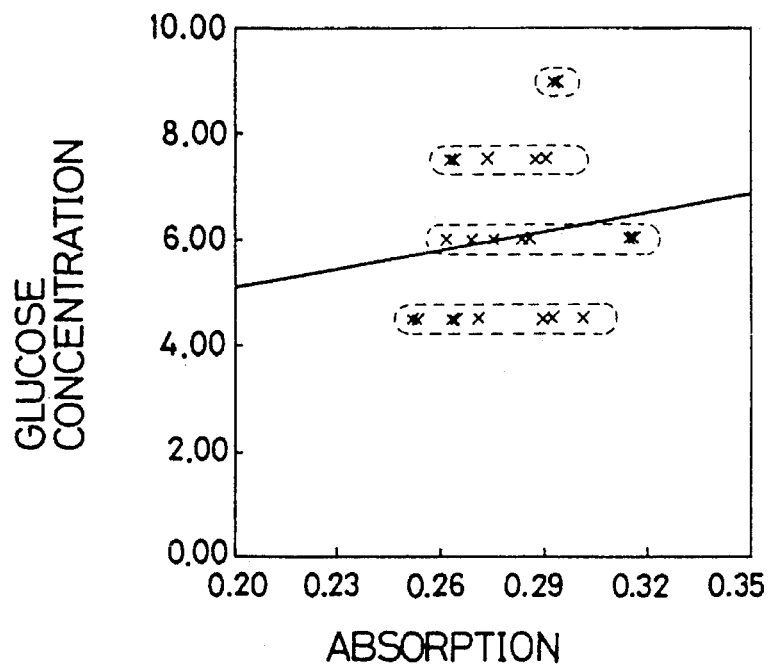
FIG. 9 is a diagram showing a correlation between absorption and glucose concentration when the temperature is not constant.

FIG. 9 shows that there is no correlation between absorption and concentration of glucose solution under the influence of temperature change in the case of a wavelength $\lambda 1$, e.g., 1595 nm where glucose maximally absorbs radiation being selected without considering a temperature characteristic.

Figure 10:
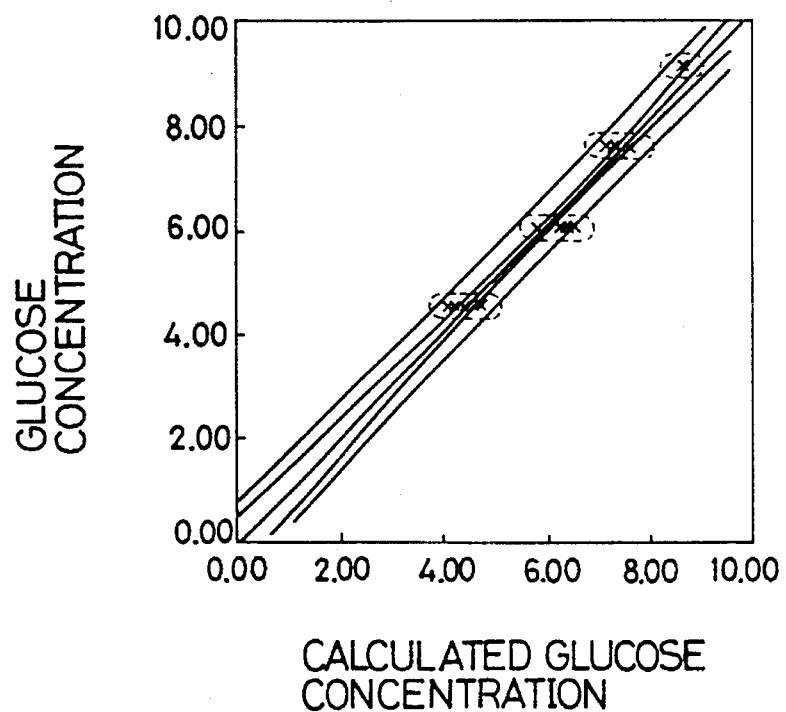
FIG. 10 is a diagram showing a correlation between glucose concentration calculated using two selected wavelengths and actual glucose concentration.

On the other hand, FIG. 10 shows that glucose concentrations calculated based on absorption of radiation of a wavelength range which allows high absorption variations as well as absorption of radiation of a wavelength range which allows high temperature characteristics corresponds with actually measured glucose concentrations regardless of temperature change.

An operation of measuring a glucose concentration in blood by use of this measuring apparatus will be described with reference to flow charts shown in FIGS. 2 and 3.

First, after a sample S to be measured (organism tissues) such as a finger is inserted into the cuff 3 while no pressing force is acting, the measurement start switch in the operation switch unit 13 is turned on, with the result that radiation of wavelengths $\lambda 1$ and $\lambda 2$ is emitted from the light emitter 4 to the sample S. The radiation transmitted through the sample S is detected by the photosensor and respective quantities of transmitted radiation of wavelengths $\lambda 1$ and $\lambda 2$ are measured (Step #1). A subroutine shown in FIG. 3 represents this measuring operation.

Radiations of wavelength $\lambda 1$ from the light emitter 4 are incident upon the photosensor 5 through the sample S and photoelectrically converted into a signal by the photosensor 5 (Step #21). This signal is amplified and filtered by the signal processor 6 (Step #23). Subsequently, the signal from the signal processor 6 is converted into a digital signal by the A/D converter 7 (Step #25). A quantity I1 of transmitted radiation of wavelength $\lambda 1$ represented by the A/D converted signal is stored in the memory of the controller 8 (Step #27).

Figure 3:
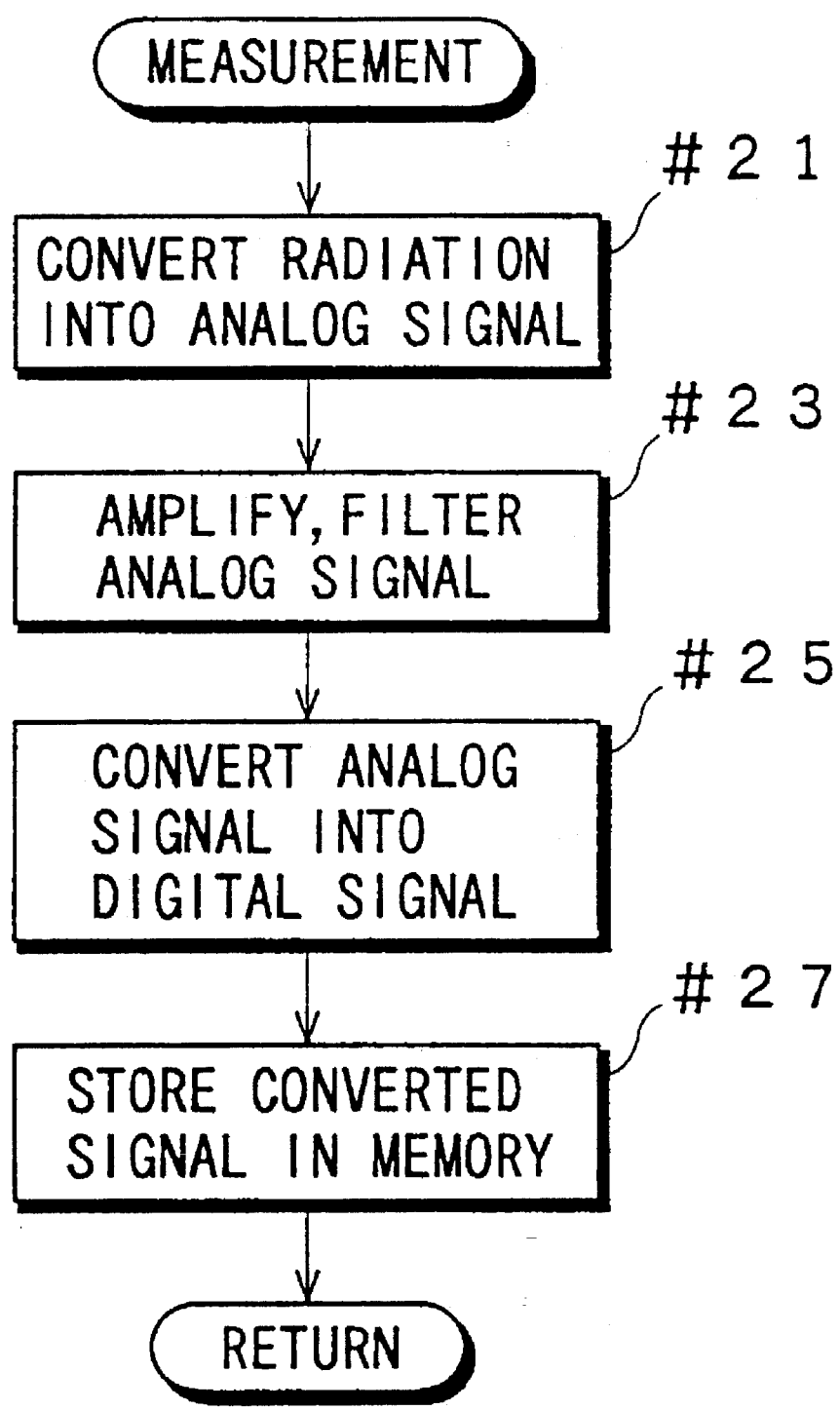
FIG. 3 is a flow chart showing a subroutine of measuring a quantity of radiation transmitted through a sample.

Similarly, when radiation of wavelength $\lambda 2$ from the light emitter 4 is incident upon the photosensor 5 through the sample S in Step #3, the subroutine shown in FIG. 3 is carried out and consequently a quantity I2 of transmitted radiation of wavelength $\lambda 2$ is stored in the memory of the controller 8.

In Step #5, air is supplied from the cuff pressure control circuit 11 to the pressing portion 30 by way of the tube 31 to inflate the pressing portion 30 of the cuff 3, so that the sample S is pressed. In this pressed state of the sample S, radiation of wavelength $\lambda 1$ from the light emitter 4 is incident upon the photosensor 5 through the sample S and then the subroutine shown in FIG. 3 is carried out. Consequently, a quantity I1' of transmitted radiation of wavelength $\lambda 1$ in the pressed state of the sample S is stored in the memory of the controller 8.

Subsequently in this pressed state of the sample S. radiation of wavelength $\lambda 2$ from the light emitter 4 is incident upon the photosensor 5 through the sample S and then the subroutine shown in FIG. 3 is carried out. Consequently, a quantity of I2' of transmitted radiation of wavelength $\lambda 1$ in the pressed state of the sample S is stored in the memory of the controller 8 (Steps #7 and #9).

In Step #11, for example a difference between the quantities I1 and I1' of transmitted radiation of wavelength $\lambda 1$ in the non-pressed and pressed states is calculated, and further a difference between the quantities I2 and I2' of transmitted radiation of wavelength $\lambda 2$ and $\lambda 2'$ in the non-pressed and pressed states is calculated. The glucose concentration Cg (glucose concentration in blood) is determined based on these calculated differences.

Subsequently, the glucose concentration is displayed in the display 9 and the cuff pressure of the pressing portion 30 of the cuff 3 is reduced to release the pressing force exerted on the sample S (Steps #13 and #15). It is then discriminated whether the print start switch in the operation switch unit 13 is on (Step #17). If the print start switch is on (YES in Step #17), the glucose concentration is printed by the printer 11 (Step #19). Then, this routine returns to Step #1 to measure a glucose concentration again.

On the other hand, if the print start switch is off (NO in Step #17), this routine returns to Step #1 without carrying out the operation of Step #19.

Although the glucose concentration measurement is repeatedly conducted in accordance with the above routine, it may be such that a remeasurement switch is provided in the operation switch unit 13 and the routine returns to Step #1 to conduct measurement only when the remeasurement switch is turned on.

Although the quantities I1' and I2' are measured after measurement of the quantities I1 and I2 in accordance with the above routine, the order of measurement may be, of course, reversed.

In this way, a glucose concentration is calculated after a temperature correction is performed using radiation of wavelength λ1 which is strongly absorbed by glucose and radiation of wavelength λ2 where light absorption depends only upon temperature and whose absorption has a correlation with the absorption of the radiation of wavelength λ1 with respect to temperature. Thus, accuracy in measuring glucose concentration can be improved.

For example if a temperature correction is applied to the glucose concentration calculated based on the quantity of transmitted radiation of wavelength λ1 which is strongly absorbed by glucose based on the quantity of transmitted radiation of wavelength λ2 as shown in FIG. 10, the corrected glucose concentration substantially corresponds with an actual glucose concentration regardless of a temperature change.

Figure 2:
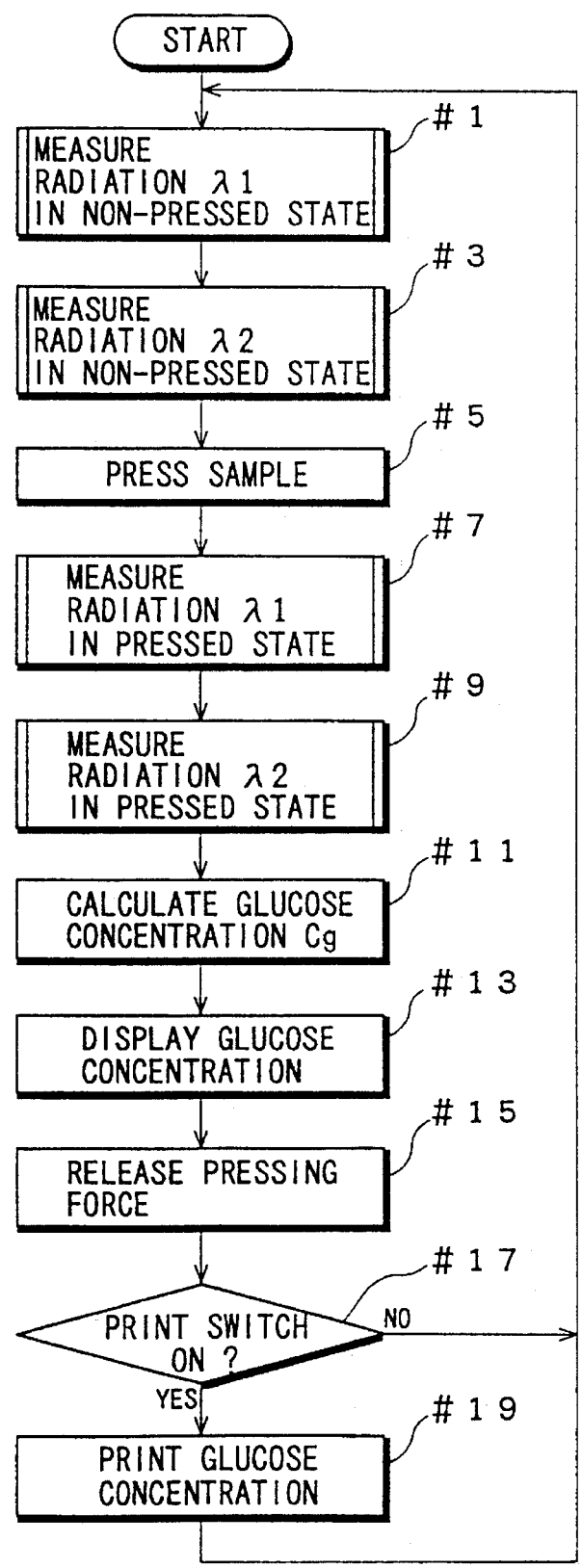
FIG. 2 is a flow chart showing a main routine of measuring glucose concentration of the measuring apparatus.

In the, routine shown in FIG. 2. there is used a technique of calculating a glucose concentration using the differences between the quantities of transmitted radiation of wavelengths λ1 and λ2 in the non-pressed and pressed states of the sample S. This suppresses a likelihood of errors in measuring glucose concentration which result from a change in blood quantity due to pulsation or a personal difference of an organism's tissues such as skins or bones, thereby further improving measurement accuracy.

More specifically, when the sample S is pressed, blood hardly flows in the sample S and thus the radiation of wavelengths λ1 is absorbed mostly by the organism's tissues such as skins and bones in this state. On the other hand, when the sample S is not pressed, blood flows in the sample S and thus the radiation of wavelength λ1 is absorbed by glucose in blood as well as the organism's tissues such as skins and bones.

Accordingly, by calculating the differences between the quantities I1 and I1' and between the quantities I2 and I2', the influence of light absorption by the organism's tissues can almost be canceled.

The quantity of radiation transmitted through the sample S is as expressed in Equation (14). whereas the quantity of radiation transmitted through the sample S in the pressed state of the sample S is as expressed in Equation (18).

$$I_\lambda' = I_{0\lambda} \cdot F_\lambda \quad \text{[Equation 18]}$$

Equation (19) is obtained when Equation (18) is substituted into Equation (14). In this way, glucose concentration in blood can be measured similar to the case where only blood is measured as a sample.

$$I_\lambda = I_\lambda' \cdot 10^{-\{\epsilon_{\omega\lambda} + \epsilon_g\lambda \cdot C_g + \epsilon_t\lambda \cdot f(\Delta t)\}d} \quad \text{[Equation 19]}$$

Further, the quantities of radiation of wavelengths λ1 and λ2 transmitted through the sample S may be measured repeatedly upon each lapse of a specified time to extract pulsation components from the respective quantities of transmitted radiation. Glucose concentration may be measured using only this pulsation component.

In this case, the pulsation components of the quantities of transmitted radiation of wavelength λ1 and λ2 are caused by a change in the blood quantity due to the pulsation of blood.

Since the influence of absorption of radiation of wavelengths λ1 and λ2 by the organism's tissues such as skins and bones can be eliminated by measuring a glucose concentration using only the pulsation component, measurement accuracy can be improved.

More specifically, if it is assumed that the length d of the optical path in Equation (1) changes by Δd when the pulsation component of blood is considered, a quantity of transmitted radiation obtained at a certain timing can be expressed as in Equation (20).

$$I_\lambda = I_{0\lambda} F_\lambda \cdot 10^{-\{\epsilon_{\omega\lambda} + \epsilon_g\lambda \cdot C_g + \epsilon_t\lambda \cdot f(\Delta t)\}(d+\Delta d)} \quad \text{[Equation 20]}$$

On the other hand, an average quantity of transmitted radiation can be expressed as Equation (21).

$$\bar{I}_\lambda = I_{0\lambda} \cdot F_\lambda \cdot 10^{-\{\epsilon_{\omega\lambda} + \epsilon_g\lambda \cdot C_g + \epsilon_t\lambda \cdot f(\Delta t)\}d} \quad \text{[Equation 21]}$$

Since a quantity of transmitted radiation can be expressed as in Equation (22) from Equations (20) and (21), the glucose concentration Cg can be calculated in the same manner as described above. Employment of such calculation obviates the need to consider the influence of tissues other than blood on transmittance as in Equations (16) and (17), thereby enabling high accuracy measurement of glucose concentration.

$$I_\lambda = \bar{I}_\lambda \cdot 10^{-\{\epsilon_{\omega\lambda} + \epsilon_g\lambda \cdot C_g + \epsilon_t\lambda \cdot f(\Delta t)\}\Delta d} \quad \text{[Equation 22]}$$

It may be appreciated to use radiation of a wavelength which allows the absorption to greatly change with glucose concentration but would vary a small amount with temperature, e.g., a wavelength in a range between 2155 nm and 2225 nm, to measure a glucose concentration, and to use radiation of a wavelength which allows the absorption to have little change with glucose concentration and a little variation with temperature, e.g., a wavelength in a range between 1200 nm and 1300 nm, to correct the influence of the organism's tissues such as skins and bones. In this case, also, it will be seen that the influence of temperature can be eliminated.

Also only radiation of wavelength which allows the absorption to have a little change with temperature may be used merely to avoid the influence of temperature difference.

Depending upon purpose of avoiding the influence of blood temperature, or of avoiding the influence of organism's tissues, or other purpose, as described above, selection is made of radiation of a wavelength which allows the absorption to greatly change with glucose concentration but have a little variance with temperature, or radiation of a wavelength which allows the absorption to vary only a little with temperature but provides a required temperature characteristic. Alternatively, it may be possible to execute two measurement ways of using the two kinds of radiation respectively.

In the foregoing embodiment, a glucose concentration calculated in accordance with an operation expression based on the data obtained by using the wavelengths λ1 and λ2. However, a glucose concentration may be calculated based on a level of received radiation of wavelength λ1 and a temperature correction may be applied to the calculated concentration using a level of received radiation of wavelength λ2.

Although glucose concentration measured using two wavelengths λ1 and λ2 selected in the foregoing embodiment, one or more wavelengths may be additionally selected and used in order to further reduce the influence of an organism's tissues and substances in blood.

Calculation may be performed by the controller 8 using a suitable operation expression. Alternatively, a ROM table containing calculation results may be provided. This alternative shortens the calculation time.

The foregoing embodiment is directed to a measuring apparatus of a non-invasive type for measuring a glucose concentration of an organism's tissues as a sample to be measured. However, the present invention can be also applicable to a measuring apparatus for measuring a glucose concentration in, for example, collected blood. In this case, the time to measure a glucose-concentration can be shortened because the pressing by the cuff 3 is not necessary.

Although the present invention has been fully described by way of example with reference to the accompanying drawings, it is to be understood that various changes and modifications will be apparent to those skilled in the art. Therefore, unless otherwise such changes and modifications depart from the scope of the present invention they should be construed as being included therein.

What is claimed is:

1. An apparatus for noninvasively measuring a glucose concentration of a sample, the apparatus comprising:

a first light source which projects at the sample radiation of a wavelength range including a first wavelength $\lambda_1$ at which absorption is dependent upon glucose concentration;

a second light source which projects at the sample radiation of a wavelength range including a second wavelength $\lambda_2$, different from the first wavelength $\lambda_1$, at which absorption has a temperature-dependent characteristic correlated with that in absorption of radiation of the first wavelength $\lambda_1$;

a photosensor which receives the two kinds of radiation which have been projected by the first and second light sources, and transmitted through or reflected by the sample, and generates a first electrical signal corresponding to a through-transmitted or reflected level of the radiation of the first wavelength $\lambda_1$ and a second electrical signal corresponding to a through-transmitted or reflected level of the radiation of the second wavelength $\lambda_2$; and a calculator which calculates a glucose concentration based on the first and second electrical signals.

2. An apparatus according to claim 1, wherein the first wavelength $\lambda1$ lies within a range between 1560 nm and 1760 nm and the second wavelength $\lambda2$ lies within a range between 1440 nm and 1560 nm.

3. An apparatus according to claim 1, wherein the first wavelength $\lambda1$ lies within a range between 2080 nm and 2230 nm and the second wavelength $\lambda2$ lies within a range between 2050 nm and 2080 nm.

4. An apparatus according to claim 1, wherein the photosensor includes an optical filter for separately receiving the radiation of the wavelength range including the first wavelength $\lambda1$ and the radiation of the wavelength range including the second wavelength $\lambda2$.

5. An apparatus according to claim 1, further comprising a pressing device which presses the sample, wherein:

the photosensor generates first and second electrical signals in a state of the sample being not pressed and first and second electrical signals in another state of the sample being pressed; and the calculator calculates a glucose concentration based on the first and second electrical signals in the non-pressed state and the first and second electrical signals in the pressed state.

6. An apparatus according to claim 1, wherein the calculator calculates a glucose concentration in consideration of a variation in the through-transmitted or reflected radiation which is caused by pulsation of blood at a measured portion when the sample is an organism.

7. An apparatus according to claim 1, wherein the first wavelength $\lambda1$ lies within a range between 2155 nm and 2225 nm and the second wavelength $\lambda2$ lies within a range between 1200 nm and 1300 nm.

8. An apparatus for noninvasively measuring a glucose concentration of a sample, the apparatus comprising:

a light source which projects at the sample radiation of a wavelength range including a first wavelength $\lambda_1$ at which absorption is dependent upon glucose concentration and a second wavelength $\lambda_2$, different from the first wavelength $\lambda_1$, at which absorption has a temperature-dependent characteristic correlated with that in absorption of radiation of the first wavelength $\lambda_1$;

a photosensor which receives the two kinds of radiation which have been projected by the light source, and transmitted through or reflected by the sample, and generates a first electrical signal corresponding to a through-transmitted or reflected level of the radiation of the first wavelength $\lambda_1$ and a second electrical signal corresponding to a through-transmitted or reflected level of the radiation of the second wavelength $\lambda_2$; and a calculator which calculates a glucose concentration based on the first and second electrical signals.

9. An apparatus according to claim 8, wherein the first wavelength $\lambda1$ lies within a range between 1560 nm and 1760 nm and the second wavelength $\lambda2$ lies within a range between 1440 nm and 1560 nm.

10. An apparatus according to claim 8, wherein the first wavelength $\lambda1$ lies within a range between 2080 nm and 2230 nm and the second wavelength $\lambda2$ lies within a range between 2050 nm and 2080 nm.

11. An apparatus according to claim 8, wherein the photosensor includes an optical filter for separately receiving the radiation of the wavelength range including the first wavelength $\lambda1$ and the radiation of the wavelength range including the second wavelength $\lambda2$.

12. An apparatus according to claim 8, further comprising a pressing device which presses the sample, wherein:

the photosensor generates first and second electrical signals in a state of the sample being not pressed and first and second electrical signals in another state of the sample being pressed; and the calculator calculates a glucose concentration based on the first and second electrical signals in the non-pressed state and the first and second electrical signals in the pressed state.

13. An apparatus according to claim 8, wherein the calculator calculates a glucose concentration in consideration of a variation in the through-transmitted or reflected radiation which is caused by pulsation of blood at a measured portion when the sample is an organism.

14. An apparatus according to claim 8, wherein the first wavelength $\lambda1$ lies within a range between 2155 nm and 2225 nm and the second wavelength $\lambda2$ lies within a range between 1200 nm and 1300 nm.

* * * * *